United States Patent [19]

Teach

[11] 4,249,931
[45] Feb. 10, 1981

[54] 5-OXY OR THIOMETHYL SUBSTITUTED OXAZOLIDINE HERBICIDE ANTIDOTES

[75] Inventor: Eugene G. Teach, El Cerrito, Calif.

[73] Assignee: Stauffer Chemical Company, Westport, Conn.

[21] Appl. No.: 49,697

[22] Filed: Jun. 18, 1979

[51] Int. Cl.³ .................... A01N 25/32; C07D 263/06
[52] U.S. Cl. ........................................ 71/88; 548/215; 71/100
[58] Field of Search ...................... 548/215; 71/88, 100

[56] References Cited

U.S. PATENT DOCUMENTS

| | | | |
|---|---|---|---|
| 3,989,503 | 11/1976 | Pallos et al. | 71/88 |
| 4,072,688 | 2/1978 | Teach | 71/88 |

Primary Examiner—Catherine L. Mills
Attorney, Agent, or Firm—Harry A. Pacini

[57] ABSTRACT

Substituted N-haloacyl oxazolidines as new compositions of matter useful as active herbicidal antidotes to protect against and decrease crop injury when used with thiolcarbamate herbicides when applied in various methods; improved herbicidal compositions and utility of said compositions to protect against and decrease phytotoxic crop injury when employing thiolcarbamate herbicides, and a two-part herbicide system consisting essentially of a first-part of one or more thiolcarbamate herbicides and a second-part of an effective antidote compound therefor, said antidote compounds of the class 5-substituted 3-acyl oxazolidines having the formula

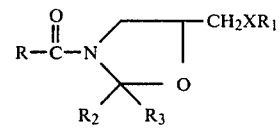

wherein X is oxygen or sulfur and $R_1$ is alkyl; R is selected from the group consisting of haloalkyl, and alkoxy carboalkyl; $R_2$ is selected from the group consisting of phenyl, p-chlorophenyl and p-bromophenyl; and $R_3$ is selected from the group consisting of hydrogen and methyl.

109 Claims, No Drawings

5-OXY OR THIOMETHYL SUBSTITUTED OXAZOLIDINE HERBICIDE ANTIDOTES

BACKGROUND OF THE INVENTION

While many herbicides are immediately toxic to a large number of weed pests, it is known that the effect of many herbicides upon important plant cultivations is either non-selective or not adequately selective. Thus, many herbicides damage not only the weeds to be controlled but, to a greater or lesser extent, the desirable cultivated plants as well. This holds true for many herbicidal compounds which have been commercially successful and are commercially available. These herbicides include types such as triazines, urea derivatives, halogenated acetanilides, carbamates, thiolcarbamates and the like. Some examples of these compounds are described in U.S. Pat. Nos. 2,913,327, 3,037,853, 3,175,897, 3,185,720, 3,198,786, 3,582,314 and 3,952,056.

The side effect of injury to a cultivated crop by various herbicides is particularly inconvenient and unfortunate. When used in the recommended amounts in the soil to control broadleaf weeds and grasses, serious malformation or stunting of the crop plants sometimes result. This abnormal growth in the crop plants results in loss of crop yield. The search continues for good selective herbicides.

Previous attempts are described to overcome this problem. The treatment of the crop seed with certain "hormonal" antagonistic agents prior to planting is described; see U.S. Pat. Nos. 3,131,509 and 3,564,768. The protective agents, as well as the herbicide, in these prior processes are largely specific to certain cultivated plant species or in the nature of the antagonistic agents. The prior antagonistic agents have not been notably successful. The aforementioned patents specifically exemplify and describe the treatment of seeds employing compounds of a different chemical class, not suggestive of the present invention.

U.S. Pat. Nos. 3,989,503, 4,072,688 and 4,124,372 disclose certain substituted oxazolidine compounds. However, none of these references anticipate or make obvious the particular compounds or the utility of the particular compounds as herbicidal antidotes for thiolcarbamate herbicides, in particular for S-n-propyl N,N-di-n-propylthiolcarbamate, S-ethyl di-n-propyl thiolcarbamate, S-isopropyl 1-(5-methyl-2-methyl-piperidine) carbothioate, S-ethyl diisobutyl thiolcarbamate, and S-ethyl cyclohexyl ethyl thiolcarbamate. None of the references anticipate or make obvious the improved herbicidal compositions for use employing N-haloacyl oxazolidines substituted in the 5-position with substituted methyloxy or methylthio moieties.

DESCRIPTION OF THE INVENTION

It has been discovered that cultivated crop plants can be protected against injury by thiolcarbamate-type herbicides, and said injury can be decreased when the thiolcarbamate-type herbicides, each alone or in mixtures or combination with other compounds, are applied in a variety of ways. Further, as an alternative effect, the tolerance of the plants, to these herbicides, can be substantially increased by adding to the soil an antidote compound of the type N-haloacyl oxazolidine substituted in the 5-position with oxy or thio containing groups, therefore, the present invention also includes a two-part herbicide system comprising a first-part of one or more thiolcarbamate herbicides and a second-part of an effective antidote compound therefore, said antidote compounds corresponding to the following formula

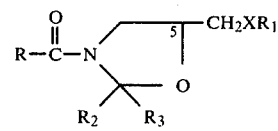

wherein X is oxygen or sulfur and $R_1$ is alkyl; R is selected from the group consisting of haloalkyl, and alkoxycarboalkyl; $R_2$ is selected from the group consisting of phenyl, p-chlorophenyl and p-bromophenyl; and $R_3$ is selected from the group consisting of hydrogen and methyl.

In the above description, the following embodiments are intended for the various substituent groups: For $R_1$ alkyl preferably includes those members which contain from 1 to 6 carbon atoms, inclusive, in both straight chain and branched chain configurations. As exemplary of the alkyl portion within the preferred embodiment are the following: Methyl, ethyl, n-propyl, isopropyl, n-butyl, sec.-butyl, isobutyl and tert.-butyl. For R as haloalkyl preferably includes those members which contain from 1 to 4 carbon atoms, inclusive, and the term "halo" includes chloro and bromo as mono, di, tri, tetra or hexa substitutions, that is from 1 to 6 halo substituents; and for R as alkoxycarboalkyl preferably includes those members having 3 to 6 carbon atoms, inclusive, such as methoxy propanoyl, methoxy ethanoyl (acetyl), ethoxy propanoyl, ethoxy ethanoyl and the like. Other substituent groups are as indicated in carbon content in the above description.

As an alternative mode of action, the compounds of this invention may interfere with the normal herbicidal action of the thiolcarbamate-type and other herbicides to render them selective in their action. The observation noted with the presence of the herein described antidote is a decrease in phytotoxicity with respect to various crops, otherwise observed when various thiolcarbamate herbicides are used for weed control. Whichever mode of action is present, the corresponding beneficial and desirable effect is the continued herbicidal effect of the thiolcarbamate against weed species present in the crop, with the accompanying decreased herbicidal effect on desired crop species. This advantage and utility will become more apparent hereinafter.

Therefore, the terms "antidote", "herbicide antidote" or "antidotal amount", is meant to describe that effect which tends to counteract the normal injurious herbicidal response that the herbicide might otherwise produce. Whether it is to be termed a remedy, interferant, protectant, antagonist or the like, will depend upon the mode of action. The mode of action is varied, but the effect, which is desirable, is the result of the method of treating the seed, soil or furrow in which a crop is planted.

The compounds of this invention represented by the above formulas can be prepared by several different procedures depending upon the starting materials.

When X is oxygen and $R_1$ is alkyl, the requisite starting material for the compounds within this invention may be prepared by amination of a 1,2-epoxy-3-alkoxy or alkenoxy propane (I) with aqueous ammonia or ammonium hydroxide to produce a 1-amino-3-alkoxy isopropanol (II). Subsequent reaction and cyclization with benzaldehyde or a substituted benzaldehyde, phenyl or substituted phenyl ketone (III), yields the N-substituted 2,2-dialkyl 5-alkoxy oxazolidine product (IV). This sequence of reactions is depicted by the following equations:

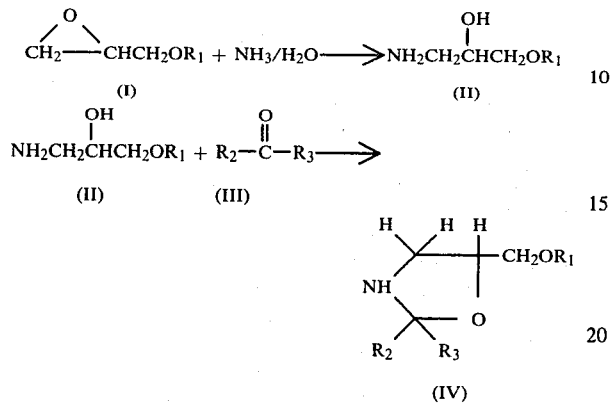

wherein $R_1$, $R_2$ and $R_3$ have the same significance as previously defined.

When X is sulfur and $R_1$ is alkyl, the requisite starting material for the compounds within this invention may be prepared by thionation with a mercaptan (VI) of epichlorohydrin (V) to produce the 1-chloro alkyl thio-2-propanol (VII), this is followed by reformation of the epoxide (VIII). Amination of the 1,2-epoxy-3-alkylthio propane (VIII) with ammonia or aqueous ammonia produce a 1-amino-3-alkylthio 2-propanol (IX). Subsequent reaction and cyclization benzaldehyde or a substituted benzaldehyde, phenyl or substituted phenyl ketone (III) yields the N-unsubstituted 2,2-dialkyl methyl oxazolidine product (X), this sequence of reactions is depicted by the following equations:

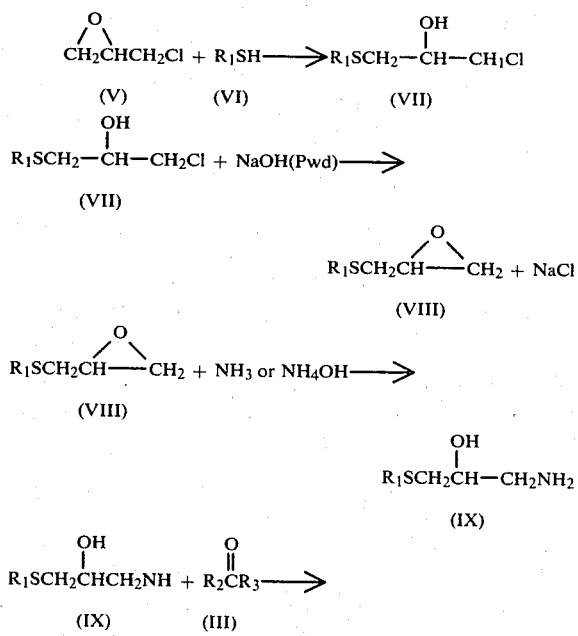

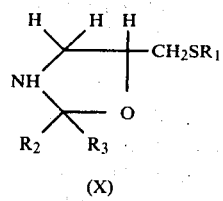

The N-acyl-substituted compounds of the invention wherein R is haloalkyl, may be prepared by direct acylation of a 5-substituted oxazolidine compound with an acid chloride, such as carboalkoxyalkanoyl chloride, alkanoyl chloride or alkoxyalkanoyl chloride, in the presence of a hydrogen chloride acceptor, such as triethylamine or an inorganic base, such as sodium hydroxide.

In the reactions above, the reactions may be performed in the presence of an inert organic solvent, such as benzene where good chemical practice dictates, a catalyst was used as specified. In some instances, a catalyst is not required. The reaction temperatures can vary from $-10°$ C. to $90°$ C. The reaction pressure may be atmospheric, subatmospheric or superatmospheric. However, for convenience of conducting the reactions, the pressure is generally atmospheric. The reaction time will, of course, vary depending upon the reactants and reaction temperature. Generally, the reaction time is from 0.25 to 24 hours. After the reaction is complete, the product is recovered by separation and the solvent evaporated. The structure is confirmed by nuclear magnetic resonance or infrared spectra.

Whereas solvent is normally employed to facilitate the reaction and aid in the work-up of the product; after filtration, extraction and drying, the product can be purified further by trituration with hexane or recrystallization from a suitable solvent. In most instances, the structure was confirmed by analytical techniques such as infrared spectroscopy, nuclear magnetic resonance, or mass spectroscopy.

Representative of the above general reaction scheme, are the following intermediate preparations employing specific sulfur containing starting materials and intermediates.

Preparation of Intermediate

1-Chloro-3-ethylthio-2-propanol

Sixty five and two tenths (65.2) grams of ethyl mercaptan was added dropwise with stirring to 92.5 grams of epichlorohydrin and 2 grams of zinc chloride in 500 milliliters of dioxane. The mixture was heated to 40° C. and the heating removed while the mixture remained at 35°–40° C. for ¾ hours. The mixture was then heated at 40° C. for 1½ hours and then to reflux at which point the temperature was 105° C. Yield after stripping was 103 grams, $n_D^{30}$ 1.4862. The product was not further purified. The structure was confirmed by infrared and nuclear magnetic resonance spectroscopy.

Preparation of Intermediate

3-Ethyl-1,2-epoxypropyl sulfide

One hundred and twenty seven (127.0) grams of 1-chloro-3-ethylthio-2-propanol was added dropwise with vigorous stirring to 82 grams of powdered NaOH in 500 milliliters of diethyl ether. The temperature was kept below 30° C. with a water bath and addition took 40 minutes. The product was filtered and the ether stripped off giving 80.8 grams of product, $n_D^{30}$ 1.4567. The structure was confirmed by infrared and nuclear magnetic resonance spectroscopy and used in subsequent reactions without purification.

Preparation of Intermediate

2-Hydroxy-3-aminopropyl ethyl sulfide

Eighty seven and eight tenths (87.8) grams of 3-ethyl-1,2-epoxypropyl sulfide was added dropwise with stirring to 1 liter of aqueous 28 percent ammonia solution, cooled to 0° C. overnight in an icebox and maintained in an ice bath. The epoxide was added over 45 minutes and the reaction mixture was allowed to warm to room temperature and stand overnight. The water and ammonia were stripped off under vacuum and the only residue distilled to give 59.1 grams of the title compound, b.p. 101°–105° C. at 1.4–2 millimeters, $n_D^{30}$ 1.4910. The structure was confirmed by infrared and nuclear magnetic resonance spectroscopy.

In preparing the oxazolidine intermediates it was found that it was unnecessary to isolate and purify the compounds before use. The volume of the oxazolidine solution was adjusted to give a 25% w/v solution (4 milliliters=1 gram) and aliquots were then used for subsequent reactions. Both the 5-oxymethyl and 5-thiomethyl substituted oxazolidines can be prepared by similar reactions.

Preparation of Intermediate

1-Amino-3-isopropoxy isopropanol

Sixty three (63.0) grams of 3-isopropoxy-1,2-epoxypropane was added dropwise with stirring to 1 liter of 28 percent aqueous ammonia, cooled to 0° C. and kept in an icebox overnight. The solution was allowed to warm to room temperature and stored in a loosely stoppered container for five days in a hood. The water and ammonia was stripped off under vacuum and the only residue distilled to give 38 grams of the title compound, b.p. 77.5° C. at 0.5 millimeters, $n_D^{30}$ 1.4200. The structure was confirmed by infrared and nuclear magnetic resonance spectroscopy.

Preparation of Intermediate

2-p-Chlorophenyl-5-methoxymethyl oxazolidine

Twelve and six tenths (12.6) grams of 1-amino-3-methoxy-2-propanol and 16.9 grams of p-chlorobenzaldehyde were combined in 150 milliliters of benzene and heated to reflux under a modified Dean-Stark apparatus until about 2.5 milliliters of water were azeotropically removed. An additional 50 milliliters of benzene was distilled over and the mixture was cooled to room temperature and the volume was adjusted to 109.2 milliliters, so that 4 milliliters=1 gram of intermediate. Aliquots of this solution were used in subsequent reactions.

Preparation of Intermediate

2-Phenyl-5-ethylthiomethyl oxazolidine

Thirteen and five tenths (13.5) grams of 2-hydroxy-3-aminopropyl ethyl sulfide and 10.6 grams of benzaldehyde were combined in 100 milliliters of benzene and refluxed under a modified Dean-Stark apparatus until about 2 milliliters of water had been azetropically removed. The mixture was cooled to room temperature and the volume adjusted to 89.2 milliliters (4 milliliters=1 gram). Aliquots of this mixture were used in subsequent reactions.

The compounds of the present invention and their preparation are more particularly illustrated by the following examples. Following the examples of preparation is a table of compounds which are prepared according to the procedures described herein. Compound numbers have been assigned to them and are used for identification throughout the balance of the specification.

EXAMPLE I

Preparation of 2-p-chlorophenyl-2(2,3-dibromopropionyl)5-methoxymethyl oxazolidine To 20.8 milliliters of 25 percent w/v, p-chlorophenyl-5-methoxymethyl oxazolidine solution in 50 milliliters of benzene was added 5 grams of 2,3-dibromopropionyl chloride. To this solution was added 1.6 grams of 50% sodium hydroxide. After washing with water, drying and removal of the benzene in vacuo, there was obtained 4.8 grams of the title compound, $n_D^{30}$ 1.5478. Analytical data supports the structure.

EXAMPLE II

Preparation of 2-p-chlorophenyl-3(2,3-dibromopropionyl)5-propoxymethyl

In a similar manner as Example I, 17.9 milliliters of 25 percent w/v, 2-p-chlorophenyl oxazolidine solution in 50 milliliters of benzene and 4.4 grams of 2,3-dibromopropionyl chloride was added 1.4 grams of 50% sodium hydroxide. After the appropriate work-up procedure, there was obtained a yield of 6.4 grams of the title compound, $n_D^{30}$ 1.5310. Analytical data supports the structure.

EXAMPLE III

Preparation of 2-p-chlorophenyl-3(3-carbomethoxypropionyl)5-propoxymethyl oxazolidine To 25.6 milliliters of 25 percent w/v, 2-p-chlorophenyl-5-propoxymethyl oxazolidine solution in 50 milliliters of benzene was added 3.8 grams of 3-carbomethoxypropionyl chloride. To this reaction mixture was added 2 grams of 50% sodium hydroxide. Upon completion of the reaction solvent, benzene, was removed in vacuo. There was obtained 6.0 grams of the title compound, $n_D^{30}$ 1.4975. Analytical data supports the structure.

EXAMPLE IV

Preparation of 2-phenyl-2(3-carbomethoxypropionyl)5-methoxymethyl oxazolidine To 19.3 milliliters of 25 percent w/v, 2-phenyl-5-methoxymethyl oxazolidine solution in 50 milliliters of benzene with 3.8 grams of 3-carbomethoxyproprionyl chloride was added 2.0 grams of 50% sodium hydroxide. After the reaction was complete the mixture was washed with water, separated, dried and the organic solvent removed in vacuo. There was obtained 6.8 grams of the title compound, $n_D^{30}$ 1.4913. Analytical data supports the structure.

EXAMPLE V

Preparation of 2-phenyl-3-chloroacetyl-5-ethylthiomethyl oxazolidine

To a reaction mixture of 10.1 milliliters of 25 percent w/v, 2-phenyl-5-ethylthiomethyl oxazolidine solution in 25 milliliters benzene, 2.5 grams of triethylamine were added dropwise. Cooling in an ice bath and vigorous stirring was maintained during the addition of the chloride and triethylamine, then allowed to stir one hour at room temperature. Upon completion of the reaction, the mixture was washed with water, dried, and the solvent removed in vacuo. There was obtained a yield of 6.0 grams of the title compound, $n_D^{30}$ 1.5410.

TABLE I

| Compound Number | R | $XR_1$ | $R_2$ | $R_3$ | Physical Constant $n_D^{30}$ |
|---|---|---|---|---|---|
| 1 | $CHCl_2$ | $OCH_3$ | p-Cl phenyl | H | 1.5530 |
| 2 | $CH_2BrCHBr$ | $OCH_3$ | p-Cl phenyl | H | 1.5478 |
| 3 | $CH_2BrCH_2$ | $OCH_3$ | p-Cl phenyl | H | 1.5341 |
| 4 | $CH_2ClCH_2$ | $OCH_3$ | p-Cl phenyl | H | 1.5248 |
| 5 | $CH_3OC(O)CH_2CH_2$ | $OCH_3$ | p-Cl phenyl | H | 1.5094 |
| 6 | $CHCl_2$ | $OC_3H_7$ | p-Cl phenyl | H | 1.5171 |
| 7 | $CH_2BrCHBr$ | $OC_3H_7$ | p-Cl phenyl | H | 1.5310 |
| 8 | $CH_2BrCH_2$ | $OC_3H_7$ | p-Cl phenyl | H | 1.5195 |
| 9 | $CH_2ClCH_2$ | $OC_3H_7$ | p-Cl phenyl | H | 1.5088 |
| 10 | $CH_3OC(O)CH_2CH_2$ | $OC_3H_7$ | p-Cl phenyl | H | 1.4975 |
| 11 | $CHCl_2$ | $OCH_3$ | phenyl | H | 1.5230 |
| 12 | $CH_2ClCH_2$ | $OCH_3$ | phenyl | H | 1.5130 |
| 13 | $CH_3OC(O)CH_2CH_2$ | $OCH_3$ | phenyl | H | 1.4913 |
| 14 | $CH_3CHCl$ | $OCH_3$ | phenyl | H | 1.5075 |
| 15 | $CHCl_2$ | $OC_3H_7$ | phenyl | H | 1.5065 |
| 16 | $CH_2BrCH_2$ | $OC_3H_7$ | phenyl | H | 1.5090 |
| 17 | $CH_2ClCH_2$ | $OC_3H_7$ | phenyl | H | 1.5010 |
| 18 | $CH_3OC(O)CH_2CH_2$ | $OC_3H_7$ | phenyl | H | 1.4868 |
| 19 | $CH_3CHCl$ | $OC_3H_7$ | phenyl | H | 1.4979 |
| 20 | $CHCl_2$ | $OCH_3$ | p-Br phenyl | H | 1.5363 |
| 21 | $CH_2BrCHBr$ | $OC_3H_7$ | p-Br phenyl | H | 1.5390 |
| 22 | $CH_3OC(O)CH_2CH_2$ | $OC_3H_7$ | p-Br phenyl | H | 1.5032 |
| 23 | $CHCl_2$ | $OC_5H_{11}$ | phenyl | H | 1.4960 |
| 24 | $CH_2BrCHBr$ | $OC_5H_{11}$ | phenyl | H | 1.5123 |
| 25 | $CH_3OC(O)CH_2CH_2$ | $OC_5H_{11}$ | phenyl | H | 1.4940 |
| 26 | $CH_2Cl$ | $SC_2H_5$ | phenyl | H | 1.5410 |
| 27 | $CH_2BrCHBr$ | $SC_2H_5$ | phenyl | H | 1.5580 |
| 28 | $CH_2BrCH_2$ | $SC_2H_5$ | phenyl | H | 1.5461 |

The herbicidal compound employed in the utility of this invention is an active thiolcarbamate herbicide of a general type. That is, it is a member of the class of herbicidally active compounds effective against a wide range of plant species, and may have no discrimination between desirable and undesirable plant species. The method of controlling vegetation comprises applying a herbicidally effective amount of the herein described herbicidal composition to the area, plant or plant locus where control is desired. The herbicidal composition as set forth in this invention include those wherein the antidote is as described above and the preferred active herbicidal compound is selected from the class of the thiolcarbamate herbicides and includes the following representative members: S-ethyl dipropyl thiolcarbamate, S-ethyl diisobutyl thiolcarbamate, S-propyl di-n-propyl thiolcarbamate, S-ethyl cyclohexyl ethyl thiolcarbamate, S-ethyl hexahydro-1H-azepine-1-carbothioate, 2,3,3-trichloroallyl N,N-diisopropyl thiolcarbamate, S-isopropyl-1-(5-ethyl-3-methylpiperidine) carbothioate and S-4-chlorobenzyl diethyl thiolcarbamate.

As an embodiment within the scope of the present invention is a two-part or package herbicide system comprising a first-part of one or more thiolcarbamate herbicides and a second-part of an antidote compound therefor. It is understood that the antidote compound is used in an effective amount to render the two-part herbicide system selective in decreasing phytotoxic effects to desired or beneficial crops and yet phytotoxic to the undesirable or unwanted vegetation. Thus the soil treated by such a system becomes extremely useful and desirable, allowing previously injured crops to be planted in said treated soil, otherwise injured by the herbicide when used alone. Hence, soil treated with herbicide and antidote as described herein is beneficial, desirable and useful.

An herbicide as used herein means a compound which controls or modifies the growth of vegetation or plants. Such controlling or modifying effects include all deviations from natural development; for example, killing, retardation, defoliation, desiccation, regulation, stunting, tillering, stimulation, dwarfing and the like. By "plants" it is meant germinant seeds, emerging seedlings and established vegetation including the roots and above-ground portions.

Evaluation Procedure and Method

Flats to be used for growing the crops and weed species were filled with loamy sand soil. Various methods of application were employed, such as pre-plant incorporation (PPI) of (1) the herbicide and antidote separately, and (2) as a tank mix (PPI-TM) with the herbicide and antidote together. The application was by incorporation, whereinafter the seeds of the crops and weeds were planted in the treated soil; application by an in-furrow (IF) treatment of the seeds and surrounding soil in which the herbicide had been applied previously to the soil.

Stock solutions of representative thiolcarbamate herbicides and antidote candidates were prepared as follows:

Herbicides

A. S-ethyl di-n-propyl thiolcarbamate—EPTC—EPTAM ® 6E-4133 mg. dissolved in 800 ml water such that 5 ml. applied to the soil from a planting flat is equivalent to 5 lb/A PPI or 3744 mg. dissolved in 600 ml of water, 5 ml. of which was equivalent to 6 lb/A PPI.

B. S-ethyl di-isobutyl thiolcarbamate—SUTAN ® 6E or S-ethyl cyclohexyl ethyl thiolcarbamate—RONEET ® 6E-390 mg. dissolved in 125 ml. water such that 5 ml. applied to the soil from a planting flat is equivalent to 3 lb/A. For 4 lb/A, 1456 mg. was dissolved in 350 ml water, such that 5 ml. was equivalent to 4 lb/A.

C. S-propyl di-n-propyl thiolcarbamate—VERNAM ®—6E (80%), the following is a listing of various stock solutions prepared, also included is the lb/A equivalence for 5 ml. pre-plant incorporated:
183 mg/150 ml $H_2O$; 5 ml = 1.25 lb/A PPI
975 mg/250 ml $H_2O$; 5 ml = 4 lb/A PPI
2632 mg/450 ml $H_2O$; 5 ml = 6 lb/A PPI D. For each candidate compound employed in the "in-furrow" method of application, 95 mg. of active ingredient was dissolved in 15 ml. of acetone with 1% Tween 20 ® (polyoxyethylene sorbitan monolaurate) such that 1.5 ml. applied to the seed and soil in the furrow in one-half of the flat was equivalent to 5 lb/A. When 1.0 lb/A is desired, 0.3 ml. was used.

E. For each candidate compound employed in the "tank mix" pre-plant incorporation test or separately applied pre-plant incorporated test, 50 mg. of active ingredient was dissolved in 100 ml. of acetone with 1% Tween 20 R such that when 10 ml. of the stock solution was further dissolved in 90 ml. of acetone, 4 ml. was equivalent to 1/20 lb/A PPI. When 39 mg. of the compound was dissolved in 10 ml. of acetone, 5 ml. was equivalent to 5 lb/A PPI, and 1 ml. was equivalent to 1 lb/A PPI. When 16 mg. was dissolved in 20 ml., 10 ml. was equivalent to 2 lb/A PPI and when 16 mg. was dissolved in 40 ml., 5 ml. was equivalent to 0.5 lb/A PPI.

In-furrow application of the antidote employed the above stock solutions. As a preparatory step, a one pint sample of soil was removed from each flat to be retained and used later to cover the seeds after treatment with the stock solutions. The soil was leveled before planting. The herbicide stock solution was applied respectively to separate flats and pre-plant incorporated in the soil from the planting flat at the equivalent rate of 1 lb/A active ingredient or the indicated rate.

Rows ¼-inch deep were made lengthwise in each treated flat preparatory to seeding. After seeding, the flats were sectioned into two equal portions using a wooden barrier and 1½ milliliters of additive stock solution I was atomized directly onto the exposed seed and soil in one-half of the flat. The untreated section of the flat served as an herbicide check and also made it possible to observe any lateral movement of the antidote through the soil. The seeds were covered with the one pint sample of untreated soil which had been removed earlier.

For tank mixes to be applied as a pre-plant incorporated application, the following solutions and procedure were employed. Five milliliters (5 ml.) of herbicide stock solutions were each mixed with five milliliters (5 ml.) of antidote candidate stock solution such that the required equivalent of the herbicide and antidote, respectively, were applied and incorporated into the soil of each flat. For pre-plant incorporation, the mixed stock solutions were injected into the soil during incorporation in a 5-gallon rotary mixer. Other stock solutions were employed at indicated rates in the tank mix procedure.

In side-by-side tests with various weed species and crops, it was found that weed control was maintained while at the same time the crop species were protected or injury decreased, when compared to a check or control flat. The control flat contained no candidate antidote compound. The following table includes those results.

All flats were placed on greenhouse benches where temperatures were maintained between 70°-90° F. The soil was watered by sprinkling to assure good plant growth. Injury ratings were taken 2 and 4 weeks after the applications were made. Individual control flats treated with the herbicide alone were included to provide a basis for determining the amount of injury reduction provided by the herbicide antidotes. The results of these tests are tabulated in Table II.

TABLE II
ANTIDOTE ACTIVITY

Application Method:
| | |
|---|---|
| In-Furrow | IF |
| Pre-Plant Incorporation | PPI |
| Pre-Plant Incorporation-Tank Mix | PPI-TM |

Crop Species:
| | |
|---|---|
| Barley | BA [Hordeum vulgare (L.)] |
| Corn | CN [Zea maize] |
| Cotton | CT [Gossypium hirsutum] |
| Milo | MO [Sorghum vulgare] |
| Rice | RC [Dryza sativa] |
| Soybeans | SOY [Glycine max] |
| Wheat | WH [Triticum aestivum] |

Weed Species:
| | |
|---|---|
| Green Foxtail | FT [Setaria viridis] |
| Johnson Grass | JG [Sorghum halepense] |
| Nutsedge | NS [Cyperus esulentus] |
| Shattercane | SC [Sorghum bicolor] |
| Watergrass | WG [Echinochloa crusgalli] |
| Wild Oats | WO [Avena fatua (L.)] |

$$\text{Result} = \frac{\text{Percent injury with antidote present}}{\text{Percent injury of herbicide alone}}$$

| Compound Number | Herbicide PPI | Antidote Method of Application | Rate (Herb. + Anti.) (lbs/A or % ST.) | Crop | % Injury Result | Weed | Result |
|---|---|---|---|---|---|---|---|
| 1 | VERNAM | IF | 6+5 | CN | 10/90 | | |
| | EPTAM | PPI | 5+5 | CN | 50/70 | WG | 100/100 |
| | | | | | | FT | 100/100 |
| 2 | VERNAM | IF | 1.25+5 | BA | 20/90 | | |
| | VERNAM | IF | 1.25+1 | BA | 30/80 | | |
| 3 | VERNAM | IF | 6+5 | SOY | 20/70 | | |
| 4 | VERNAM | IF | 6+5 | SOY | 30/70 | | |
| | | IF | 5+5 | SOY | 30/60 | | |
| 5 | VERNAM | IF | 6+5 | SOY | 30/70 | | |
| | VERNAM | IF | .5+1 | SOY | 20/60 | WG | 95/95 |
| | | | | | | FT | 95/95 |
| | | | 5+5 | SOY | 0/60 | WG | 95/95 |
| | | | | | | FT | 95/95 |
| 6 | VERNAM | IF | 6+5 | CN | 40/90 | | |
| 7 | VERNAM | IF | 1.25+5 | BA | 30/90 | | |
| | | IF | 1.25+1 | BA | 30/80 | FT | 70/70 |
| | | | | | | WO | 95/95 |
| 8 | VERNAM | IF | 1.25+5 | BA | 75/90 | | |
| 9 | VERNAM | IF | 6+5 | SOY | 60/70 | | |
| 10 | VERNAM | IF | 6+5 | SOY | 10/70 | | |
| | | IF | 5+1 | SOY | 40/60 | WG | 95/95 |
| | | | | | | FT | 95/95 |

TABLE II-continued

| Compound Number | Herbicide PPI | Antidote Method of Application | Rate (Herb. + Anti.) (lbs/A or % ST.) | Crop | % Injury Result | Weed | Result |
|---|---|---|---|---|---|---|---|
| 11 | VERNAM | IF | 6+5 | CN | 0/90 | | |
| | SUTAN | PPI-TM | 6+1 | CT | 10/50 | JG | 100/100 |
| | | | | | | NS | 90/90 |
| | | PPI-TM | 6+5 | CT | 0/50 | JG | 100/100 |
| | | | | | | NS | 90/90 |
| | EPTAM | PPI | 5+0.5 | CN | 50/70 | WG | 100/100 |
| | | | | | | FT | 100/100 |
| | | | 5+5 | CN | 0/70 | WG | 100/100 |
| | | | | | | FT | 100/100 |
| 12 | VERNAM | IF | 6+5 | CN | 80/90 | | |
| 13 | VERNAM | IF | 6+5 | SOY | 30/70 | | |
| | | IF | 5+5 | SOY | 30/60 | WG | 95/95 |
| | | | | | | FT | 95/95 |
| 14 | VERNAM | IF | 6+5 | SOY | 30/70 | | |
| | | IF | 5+5 | SOY | 30/60 | WG | 95/95 |
| | | | | | | FT | 95/95 |
| 15 | VERNAM | IF | 6+5 | CN | 10/90 | | |
| | EPTAM | PPI | 5+5 | CN | 0/70 | WG | 100/100 |
| | | | | | | FT | 100/100 |
| 16 | SUTAN | PPI-TM | 6+1 | CT | 20/50 | JG | 100/100 |
| | | | | | | NS | 90/90 |
| 17 | VERNAM | IF | 6+5 | SOY | 30/70 | | |
| 18 | VERNAM | IF | 6+5 | SOY | 50/70 | | |
| 19 | VERNAM | IF | 6+5 | SOY | 50/70 | | |
| | SUTAN | PPI-TM | 6+5 | CT | 40/50 | JG | 100/100 |
| | | | | | | NS | 90/90 |
| 20 | VERNAM | PPI | 1.25+5 | MO | 45/100 | | |
| | RONEET | IF | 3+1 | MO | 40/75 | FT | 80/80 |
| | | | | | | SC | 95/95 |
| | SUTAN | PPI-TM | 6+1 | CT | 40/50 | JG | 100/100 |
| | | | | | | NS | 90/90 |
| | RONEET | PPI-TM | 3+5 | MO | 30/80 | WG | 100/100 |
| | | | | | | FT | 100/100 |
| 21 | SUTAN | PPI-TM | 6+1 | CT | 40/50 | JG | 100/100 |
| | | | | | | NS | 90/90 |
| 22 | VERNAM | IF | 6+5 | SOY | 30/70 | | |
| | VERNAM | IF | 5+5 | SOY | 30/60 | WG | 95/95 |
| | | | | | | FT | 95/95 |
| 23 | VERNAM | IF | 1.25+5 | WH | 80/90 | | |
| 24 | VERNAM | IF | 1.25+5 | WH | 80/100 | | |
| | | | | BA | 75/90 | | |
| 25 | VERNAM | IF | 6+5 | SOY | 40/70 | | |
| 26 | VERNAM | IF | 6+5 | CN | 0/90 | | |
| | EPTAM | PPI-TM | 5+5 | CN | 0/85 | WG | 98/98 |
| | | | | | | JG | 98/98 |
| 27 | VERNAM | IF | 1.25+5 | BA | 30/85 | | |
| | | PPI-TM | 1.25+5 | WH | 60/80 | WG | 90/90 |
| 28 | VERNAM | IF | 1.25+5 | BA | 60/85 | | |
| | | IF | 6+5 | CN | 60/90 | | |

The compounds and compositions of this invention were employed in effective herbicidal compositions comprising the antidote and a thiolcarbamate herbicide as described hereinabove. The herbicidal compositions were tested in the above manner.

A preferred herbicidal composition consists essentially of a thiolcarbamate herbicide and an antidotally effective amount of an antidote compound therefor corresponding to the formula described hereinabove and known as 5-oxy or 5-thio methyl substituted haloacyl oxazolidines.

The compositions of the present invention for the protection of cultivated crop plants comprise the active herbicidal compound and an antidote therefor selected from the above-described compounds. The compositions of herbicide and antidote can be prepared by conventional methods through the thorough mixing and grinding of the active herbicide agents and the antidote with suitable carriers and/or other distribution media, possibly with the addition of dispersion agents or solvents.

The antidote compounds and compositions of the present invention can be used in any convenient form. A solvent or inert carrier is not necessary in view of low volume spray technology which permits the use of neat technical grade materials as sprays. Thus, the antidote compounds and composition with the thiolcarbamate herbicide can be formulated into emulsifiable liquids, emulsifiable concentrates, liquid, wettable powder, powders, granular or any other convenient form. In its preferred form, a non-phytotoxic quantity of an herbicidal antidote compound is admixed with a selected herbicide and incorporated into the soil prior to or after planting the seed. It is to be understood, however, that the herbicide can be incorporated into the soil and thereafter the antidote compound can be incorporated into the soil. Moreover, the crop seed itself can be treated with a non-phytotoxic quantity of the compound and planted into the soil which has been treated with herbicide, or untreated with the herbicide and subsequently treated with the herbicide. The addition of the antidote compound does not affect the herbicidal activity of the herbicide. The alternative methods of application have been exemplified in the above examples.

The amount of antidote compound present can range between about 0.001 to about 30 parts by weight of antidote compound described herein per each part by weight of herbicide. The exact amount of antidote compound will usually be determined on economic ratios for the most effective amount usable. It is understood that a non-phytotoxic, but effective quantity of antidote compound will be employed in the herbicidal compositions and methods described herein.

After treatment with the antidote and herbicide there is obtained as a resultant thereof, soil which is novel in composition. Said soil is improved in its capability to grow crops and to offer weed control. Further, said soil treated with herbicide and antidote has the particular utility for allowing seeds of crops otherwise injured by the herbicide to be planted and grown. The herbicide has its utility in controlling undesirable vegetation; the antidote compound decreases the injury from the herbicide upon the crop species, and the soil treated with herbicide and antidote compound provides an improved media to grow the crop in the presence of an otherwise injurious herbicide.

In the utility of the present antidote compounds and improved herbicide system, the thiolcarbamate can be applied to the soil. Application of the herbicide to the soil can take place by pre-plant incorporation. In conjunction with the prior application of the herbicide employing the present invention, crop seeds are planted. Seed planting is followed by application of the antidote as a preemergence surface application. This sequence of application of herbicide, seed planting and antidote is unusual and fully effective in decreasing injury to the plant crop, otherwise injured by the thiolcarbamate herbicide.

What is claimed is:

1. Compounds according to the formula

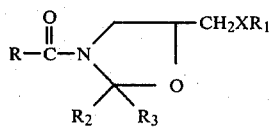

wherein X is oxygen or sulfur and $R_1$ is alkyl containing from 1 to 6 carbon atoms, inclusive; R is selected from the group consisting of haloalkyl containing from 1 to 4 carbon atoms, inclusive, and the term halo includes chloro and bromo and alkoxycarboalkyl containing 3 to 6 carbon atoms, inclusive; $R_2$ is selected from the group consisting of phenyl, p-chlorophenyl and p-bromophenyl; and $R_3$ is selected from the group consisting of hydrogen and methyl.

2. A compound according to claim 1 in which X is oxygen, $R_1$ is alkyl, R is haloalkyl, $R_2$ is p-chlorophenyl and $R_3$ is hydrogen.

3. A compound according to claim 2 in which R is dichloromethyl and $R_1$ is methyl.

4. A compound according to claim 2 in which R is 1,2-dibromoethyl and $R_1$ is methyl.

5. A compound according to claim 2 in which R is 2-bromoethyl and $R_1$ is methyl.

6. A compound according to claim 2 in which R is 2-chloroethyl and $R_1$ is methyl.

7. A compound according to claim 2 in which R is dichloromethyl and $R_1$ is propyl.

8. A compound according to claim 2 in which R is 1,2-dibromoethyl and $R_1$ is propyl.

9. A compound according to claim 2 in which R is 2-bromoethyl and $R_1$ is propyl.

10. A compound according to claim 2 in which R is 2-chloroethyl and $R_1$ is propyl.

11. A compound according to claim 1 in which X is oxygen, $R_1$ is alkyl, R is alkoxycarboalkyl, $R_2$ is p-chlorophenyl and $R_3$ is hydrogen.

12. A compound according to claim 11 in which R is methoxypropanoyl and $R_1$ is methyl.

13. A compound according to claim 11 in which R is methoxypropanoyl and $R_1$ is propyl.

14. A compound according to claim 1 in which X is oxygen, $R_1$ is alkyl, R is haloalkyl, $R_2$ is phenyl and $R_3$ is hydrogen.

15. A compound according to claim 14 in which R is dichloromethyl and $R_1$ is methyl.

16. A compound according to claim 14 in which R is 2-chloroethyl and $R_1$ is methyl.

17. A compound according to claim 14 in which R is 1-chloroethyl and $R_1$ is methyl.

18. A compound according to claim 14 in which R is dichloromethyl and $R_1$ is propyl.

19. A compound according to claim 14 in which R is 2-bromomethyl and $R_1$ is propyl.

20. A compound according to claim 14 in which R is 2-chloroethyl and $R_1$ is propyl.

21. A compound according to claim 14 in which R is 1-chloroethyl and $R_1$ is propyl.

22. A compound according to claim 14 in which R is dichloroethyl and $R_1$ is methyl.

23. A compound according to claim 14 in which R is 1,2-dibromoethyl and $R_1$ is propyl.

24. A compound according to claim 1 in which X is oxygen, $R_1$ is carboalkoxyalkyl, $R_2$ is phenyl and $R_3$ is hydrogen.

25. A compound according to claim 24 in which R is methoxypropanoyl and $R_1$ is methyl.

26. A compound according to claim 24 in which R is methoxypropanoyl and $R_1$ is propyl.

27. A compound according to claim 24 in which R is methoxypropanoyl and $R_1$ is pentyl.

28. A compound according to claim 2 in which X is oxygen, $R_1$ is alkyl, R is haloalkyl, $R_2$ is p-bromophenyl and $R_3$ is hydrogen.

29. A compound according to claim 28 in which R is dichloromethyl and $R_1$ is methyl.

30. A compound according to claim 28 in which R is 1,2-dibromoethyl and $R_1$ is propyl.

31. A compound according to claim 1 in which X is oxygen, $R_1$ is alkyl, R is alkoxycarboalkyl, $R_2$ is p-bromophenyl and $R_3$ is hydrogen.

32. A compound according to claim 31 in which R is methoxypropanoyl and $R_1$ is propyl.

33. A compound according to claim 1 in which X is sulfur, $R_1$ is alkyl, R is haloalkyl, $R_2$ is phenyl and $R_3$ is hydrogen.

34. A compound according to claim 33 in which R is dichloromethyl and $R_1$ is ethyl.

35. A compound according to claim 33 in which R is 1,2-dibromoethyl and $R_1$ is ethyl.

36. A compound according to claim 31 in which R is 2-bromoethyl and $R_1$ is ethyl.

37. A herbicidal composition consisting essentially of a thiolcarbamate herbicide and a non-phytotoxic antidotally effective amount of an antidote compound therefor corresponding to the formula

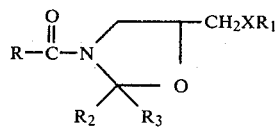

wherein X is oxygen or sulfur and $R_1$ is alkyl containing from 1 to 6 carbon atoms, inclusive; R is selected from the group consisting of haloalkyl containing from 1 to 4 carbon atoms, inclusive, and the term halo includes chloro and bromo and alkoxycarboalkyl containing 3 to 6 carbon atoms, inclusive; $R_2$ is selected from the group consisting of phenyl, p-chlorophenyl and p-bromophenyl; and $R_3$ is selected from the group consisting of hydrogen and methyl.

38. The herbicidal composition according to claim 27 in which X is oxygen, $R_1$ is alkyl, R is haloalkyl, $R_2$ is p-chlorophenyl and $R_3$ is hydrogen.

39. The herbicidal composition according to claim 38 in which R is dichloromethyl and $R_1$ is methyl.

40. The herbicidal composition according to claim 38 in which R is 1,2-dibromoethyl and $R_1$ is methyl.

41. The herbicidal composition according to claim 38 in which R is 2-bromoethyl and $R_1$ is methyl.

42. The herbicidal composition according to claim 38 in which R is 2-chloroethyl and $R_1$ is methyl.

43. The herbicidal composition according to claim 38 in which R is dichloromethyl and $R_1$ is propyl.

44. The herbicidal composition according to claim 38 in which R is 1,2-dibromoethyl and $R_1$ is propyl.

45. The herbicidal composition according to claim 38 in which R is 2-bromoethyl and $R_1$ is propyl.

46. The herbicidal composition according to claim 38 in which R is 2-chloroethyl and $R_1$ is propyl.

47. The herbicidal composition according to claim 37 in which X is oxygen, $R_1$ is alkyl, R is alkoxycarboalkyl, $R_2$ is p-chlorophenyl and $R_3$ is hydrogen.

48. The herbicidal composition according to claim 47 in which R is methoxypropanoyl and $R_1$ is methyl.

49. The herbicidal composition according to claim 47 in which R is methoxypropanoyl and $R_1$ is propyl.

50. The herbicidal composition according to claim 37 in which X is oxygen, $R_1$ is alkyl, R is haloalkyl, $R_2$ is phenyl and $R_3$ is oxygen.

51. The herbicidal composition according to claim 50 in which R is dichloromethyl and $R_1$ is methyl.

52. The herbicidal composition according to claim 50 in which R is 2-chloroethyl and $R_1$ is methyl.

53. The herbicidal composition according to claim 50 in which R is 1-chloroethyl and $R_1$ is methyl.

54. The herbicidal composition according to claim 50 in which R is dichloromethyl and $R_1$ is propyl.

55. The herbicidal composition according to claim 50 in which R is 2-bromoethyl and $R_1$ is propyl.

56. The herbicidal composition according to claim 50 in which R is 2-chloroethyl and $R_1$ is propyl.

57. The herbicidal composition according to claim 50 in which R is 1-chloroethyl and $R_1$ is propyl.

58. The herbicidal composition according to claim 50 in which R is dichloromethyl and $R_1$ is methyl.

59. The herbicidal composition according to claim 50 in which R is 1,2-dibromoethyl and $R_1$ is propyl.

60. The herbicidal composition according to claim 37 in which X is oxygen, $R_1$ is carboalkoxyalkyl, $R_2$ is phenyl and $R_3$ is hydrogen.

61. The herbicidal composition according to claim 60 in which R is methoxypropanoyl and $R_1$ is methyl.

62. The herbicidal composition according to claim 60 in which R is methoxypropanoyl and $R_1$ is propyl.

63. The herbicidal composition according to claim 60 in which R is methoxypropanoyl and $R_1$ is pentyl.

64. The herbicidal composition according to claim 37 in which X is oxygen, $R_1$ is alkyl, R is haloalkyl, $R_2$ is p-bromophenyl and $R_3$ is hydrogen.

65. The herbicidal composition according to claim 64 in which R is dichloromethyl and $R_1$ is methyl.

66. The herbicidal composition according to claim 64 in which R is 1,2-dibromoethyl and $R_1$ is propyl.

67. The herbicidal composition according to claim 37 in which X is oxygen, $R_1$ is alkyl, R is alkoxycarboalkyl, $R_2$ is p-bromophenyl and $R_3$ is hydrogen.

68. The herbicidal composition according to claim 67 in which R is methoxypropanoyl and $R_1$ is propyl.

69. The herbicidal composition according to claim 37 in which X is sulfur, $R_1$ is alkyl, R is haloalkyl, $R_2$ is phenyl and $R_3$ is hydrogen.

70. The herbicidal composition according to claim 69 in which R is dichloromethyl and $R_1$ is ethyl.

71. The herbicidal composition according to claim 69 in which R is 1,2-dibromoethyl and $R_1$ is ethyl.

72. The herbicidal composition according to claim 69 in which R is 2-bromoethyl and $R_1$ is ethyl.

73. The method of decreasing injury to crops, said injury due to a thiolcarbamate herbicide comprising application to the soil in which said crop is to be planted and grown, a non-phytotoxic antidotally effective amount of an antidote compound corresponding to the formula

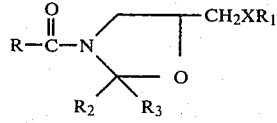

wherein X is oxygen or sulfur and $R_1$ is alkyl containing from 1 to 6 carbon atoms, inclusive; R is selected from the group consisting of haloalkyl containing from 1 to 4 carbon atoms, inclusive, and the term halo include chloro and bromo and alkoxycarboalkyl containing 3 to 6 carbon atoms, inclusive; $R_2$ is selected from the group consisting of phenyl, p-chlorophenyl and p-bromophenyl; and $R_3$ is selected from the group consisting of hydrogen and methyl.

74. The method according to claim 73 in which X is oxygen, $R_1$ is alkyl, R is haloalkyl, $R_2$ is p-chlorophenyl and $R_3$ is hydrogen.

75. The method according to claim 74 in which R is dichloromethyl and $R_1$ is methyl.

76. The method according to claim 74 in which R is 1,2-dibromoethyl and $R_1$ is methyl.

77. The method according to claim 74 in which R is 2-bromoethyl and $R_1$ is methyl.

78. The method according to claim 74 in which R is 2-chloroethyl and $R_1$ is methyl.

79. The method according to claim 74 in which R is dichloromethyl and $R_1$ is propyl.

80. The method according to claim 74 in which R is 1,2-dibromoethyl and $R_1$ is propyl.

81. The method according to claim 74 in which R is 2-bromoethyl and $R_1$ is propyl.

82. The method according to claim 74 in which R is 2-chloroethyl and $R_1$ is propyl.

83. The method according to claim 73 in which X is oxygen, $R_1$ is alkyl, R is alkoxycarboalkyl, $R_2$ is p-chlorophenyl and $R_3$ is hydrogen.

84. The method according to claim 83 in which R is methoxypropanoyl and $R_1$ is methyl.

85. The method according to claim 83 in which R is methoxypropanoyl and $R_1$ is propyl.

86. The method according to claim 73 in which X is oxygen, $R_1$ is alkyl, R is haloalkyl, $R_2$ is phenyl and $R_3$ is hydrogen.

87. The method according to claim 86 in which R is dichloromethyl and $R_1$ is methyl.

88. The method according to claim 86 in which R is 2-chloroethyl and $R_1$ is methyl.

89. The method according to claim 86 in which R is 1-chloroethyl and $R_1$ is methyl.

90. The method according to claim 86 in which R is dichloromethyl and $R_1$ is propyl.

91. The method according to claim 86 in which R is 2-bromoethyl and $R_1$ is propyl.

92. The method according to claim 86 in which R is 2-chloroethyl and $R_1$ is propyl.

93. The method according to claim 86 in which R is 1-chloroethyl and $R_1$ is propyl.

94. The method according to claim 86 in which R is dichloroethyl and $R_1$ is methyl.

95. The method according to claim 86 in which R is 1,2-dibromoethyl and $R_1$ is propyl.

96. The method according to claim 73 in which X is oxygen, $R_1$ is carboalkoxyalkyl, $R_2$ is phenyl and $R_3$ is hydrogen.

97. The method according to claim 96 in which R is methoxypropanoyl and $R_1$ is methyl.

98. The method according to claim 96 in which R is methoxypropanoyl and $R_1$ is propyl.

99. The method according to claim 96 in which R is methoxypropanoyl and $R_1$ is pentyl.

100. The method according to claim 73 in which X is oxygen, $R_1$ is alkyl, R is haloalkyl, $R_2$ is p-bromophenyl and $R_3$ is hydrogen.

101. The method according to claim 100 in which R is dichloromethyl and $R_1$ is methyl.

102. The method according to claim 100 in which R is 1,2-dibromoethyl and $R_1$ is propyl.

103. The method according to claim 73 in which X is oxygen, $R_1$ is alkyl, R is alkoxycarboalkyl, $R_2$ is p-bromophenyl and $R_3$ is hydrogen.

104. The method according to claim 103 in which R is methoxypropanoyl and $R_1$ is propyl.

105. The method according to claim 73 in which X is sulfur, $R_1$ is alkyl, R is haloalkyl, $R_2$ is phenyl and $R_3$ is hydrogen.

106. The method according to claim 105 in which R is dichloromethyl and $R_1$ is ethyl.

107. The method according to claim 105 in which R is 1,2-dibromoethyl and $R_1$ is ethyl.

108. The method according to claim 105 in which R is 2-bromoethyl and $R_1$ is ethyl.

109. The method of decreasing injury to crops, said injury due to a thiolcarbamate herbicide, comprising applying into the seed furrow to the seed and adjacent soil in the open furrow prior to covering to achieve a planted state, a non-phytotoxic antidotally effective amount of a compound corresponding to the formula

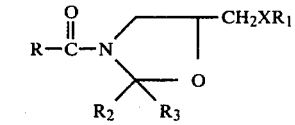

wherein X is oxygen or sulfur and $R_1$ is alkyl containing from 1 to 6 carbon atoms, inclusive; R is selected from the group consisting of haloalkyl containing from 1 to 4 carbon atoms, inclusive, and the term halo includes chloro and bromo and alkoxycarboalkyl containing 3 to 6 carbon atoms, inclusive; $R_2$ is selected from the group consisting of phenyl, p-chlorophenyl and p-bromophenyl; and $R_3$ is selected from the group consisting of hydrogen and methyl.

* * * * *

UNITED STATES PATENT AND TRADEMARK OFFICE
CERTIFICATE OF CORRECTION

PATENT NO. : 4,249,931
DATED : February 10, 1981
INVENTOR(S) : Eugene G. Teach

It is certified that error appears in the above-identified patent and that said Letters Patent is hereby corrected as shown below:

Claim 38 should read as follows:

38. The herbicidal composition according to Claim 37 in which X is oxygen, $R_1$ is alkyl, R is haloalkyl, $R_2$ is p-chlorophenyl and $R_3$ is hydrogen.

Signed and Sealed this

Ninth Day of November 1982

[SEAL]

Attest:

GERALD J. MOSSINGHOFF

Attesting Officer   Commissioner of Patents and Trademarks